United States Patent [19]

Schoendorfer et al.

[11] Patent Number: 5,053,127
[45] Date of Patent: * Oct. 1, 1991

[54] CONTINUOUS CENTRIFUGATION SYSTEM AND METHOD FOR DIRECTLY DERIVING INTERMEDIATE DENSITY MATERIAL FROM A SUSPENSION

[75] Inventors: Donald W. Schoendorfer, Santa Ana; Claude E. Berthe, San Dimas, both of Calif.

[73] Assignee: William F. McLaughlin, Newport Beach, Calif.

[*] Notice: The portion of the term of this patent subsequent to Oct. 11, 2005 has been disclaimed.

[21] Appl. No.: 526,568

[22] Filed: May 21, 1990

Related U.S. Application Data

[63] Continuation of Ser. No. 256,234, Oct. 11, 1988, Pat. No. 4,944,883, which is a continuation of Ser. No. 2,804, Jan. 13, 1987, abandoned.

[51] Int. Cl.$^5$ .......................... B04B 1/02; B01D 45/12
[52] U.S. Cl. .................................... 210/196; 210/194; 210/369; 210/378; 210/380.1; 210/398; 494/35; 494/77
[58] Field of Search ............... 210/781, 782, 787, 789, 210/805, 194, 196, 369, 378, 380.1, 360.1, 398, 399, 321.68; 604/4-6; 422/101; 127/19; 209/148; 494/10, 20, 31, 35, 37, 44, 45, 76, 77, 78

[56] References Cited

U.S. PATENT DOCUMENTS

| | | | |
|---|---|---|---|
| 2,898,037 | 8/1959 | Dega | 494/60 |
| 3,022,937 | 2/1962 | Dega | 494/60 |
| 3,519,201 | 7/1970 | Eisel | 494/14 |
| 3,656,123 | 4/1972 | Judson | 604/6 |
| 3,955,755 | 5/1976 | Breillatt | 494/10 |
| 4,262,840 | 4/1981 | Gronert | 494/24 |
| 4,341,343 | 7/1982 | Beckman | 494/84 |
| 4,350,156 | 9/1982 | Malchesky et al. | 210/434 |
| 4,530,691 | 7/1985 | Brown | 494/45 |
| 4,636,193 | 1/1987 | Cullis | 494/45 |
| 4,680,025 | 7/1987 | Kruger et al. | 604/6 |
| 4,713,176 | 12/1987 | Schoendorfer et al. | 210/782 |
| 4,734,089 | 3/1988 | Cullis | 494/45 |
| 4,755,300 | 7/1988 | Fischel et al. | 210/782 |
| 4,776,964 | 10/1988 | Schoendorfer et al. | 210/782 |
| 4,790,942 | 12/1988 | Shmidt et al. | 210/321.68 |
| 4,911,833 | 3/1990 | Schoendorfer et al. | 210/321.68 |
| 4,944,883 | 7/1990 | Schoendorfer et al. | 210/782 |

Primary Examiner—W. Gary Jones
Attorney, Agent, or Firm—Daniel D. Ryan; Bradford R. L. Price; Paul C. Flattery

[57] ABSTRACT

A system for continuously esparating lighter and intermediate density matter, such as plasma rich in platelets from whole blood moves blood through a diverging centrifugation gap between inner and outer walls of a rotor rotating about a central axis within an outer housing. The centrifugation action creates layered flow along an intermediate section. However by crating trailing wakes in the gap between the rotor and housing, localized remixing patterns tending to move in the opposite direction are induced in the layered matter. Platelet rich plasma may then be extracted through adjacent platelet concentrate ports on the inner wall of the rotor. An interior passageway system passes the platelet rich plasma to a platelet concentrate reservoir. Recirculation of blood in the rotor-housing gap between the output and input, and pumping action provided by the diverging centrifugation gap, aid in enhancing throughput and concentration levels. Prior to the centrifugation gap an initial narrow gap section is employed to limit backward propagation of the induced circulatory patterns.

16 Claims, 6 Drawing Sheets

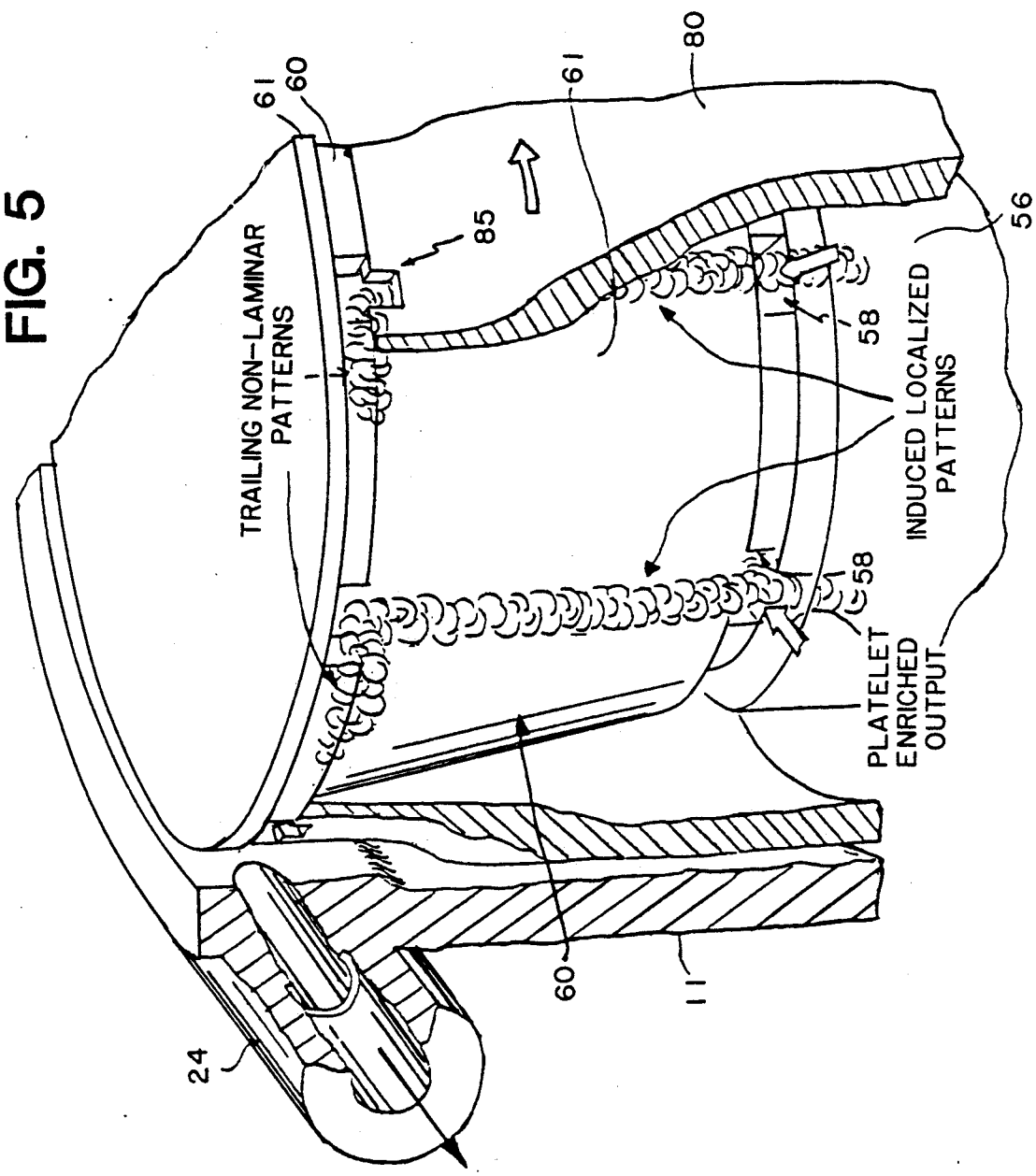

CONTINUOUS CENTRIFUGATION SYSTEM AND METHOD FOR DIRECTLY DERIVING INTERMEDIATE DENSITY MATERIAL FROM A SUSPENSION

This is a continuation of copending application Ser. No. 07/256,234 filed on 10/11/88, now U.S. Pat. No. 4,944,883, which in turn is a continuation of application Ser. No. 07/002,804, filed 1/13/87, now abandoned.

BACKGROUND OF THE INVENTION

Centrifugation is well known as a technique for separation of the constituents of a liquid suspension where the constituents have slight differences in density. Centrifugation systems are widely used in biomedical applications, one of the most important of which pertains to fractionation of the constituents of blood, which is a delicate and complex substance carrying suspended cellular and other matter of relatively small density differences. When blood samples are taken, they are often separated under high centrifugal forces by spinning at extremely high rotational velocities, such as 5,000 r.p.m. and high separation forces, such as 5,000 g, for 5–10 minutes. This produces, in the sample, layering of heaviest density red and white cell matter relative to the lightest density constituent, plasma, with a thin layer (sometimes called the "buffy coat") of platelets and white blood cells between. Specific cell types can be removed from a centrifuged bag by expressing the separated zones into individual containers.

While centrifugation is commonly carried out as a batch process, there are many continuous centrifugation systems in general use, although those suitable for blood handling are specially adapted for that purpose. When it is desired to extract an intermediate density constituent in a continuous process, a probe or knife edge at the appropriate position can be used for separation of a selected layer in a continuous centrifugation machine. Such systems are complex, particularly where the intermediate density layer is present only in a low proportion. Chromatographic techniques, which separate constituents successively with time, are also known but are again complex.

For extracting platelets from whole blood, an improved system has recently been devised that is the subject of a patent application entitled "CLOSED HEMAPHERESIS SYSTEM AND METHOD", U.S. Ser. No. 644,032, filed Aug. 24, 1984, by Donald W. Schoendorfer et al. In accordance with this system and method, platelet rich plasma is separated from blood by a first step in which blood is fed into a biologically closed structure having an interior double-walled rotor within a concentric housing. The preferential flow path is between the walls of the rotor, as opposed to the path between the outside of the rotor and the housing, so that centrifugal layering and separation of platelet rich plasma are established within the rotor. The platelet rich plasma may then be filtered in a rotary membrane system to the desired final platelet concentration, deriving plasma as an added product. The size, efficiency and simplicity of this system enable the operative parts to be fabricated as low cost disposables. The system is also operable in real time during a donation procedure to extract the platelet concentrate output while returning the remaining constituents of the blood to a patient or donor. The work leading to the present invention was undertaken to obtain important gains in platelet concentrate levels, efficiency and throughput.

Obtaining blood platelet concentrations represents a particularly critical example of the problem of extracting an intermediate density substance from both lighter and denser matter in a liquid suspension. Blood platelets are used for analytical, therapeutic and other purposes. In modern applications it is highly desirable to reinfuse platelet-depleted blood into a donor in a procedure using disposable separators and taking a minimum amount of time. Automated or semi-automated plateletpheresis systems, such as the Model V-50 of Haemonetics Corporation, the I.B.M. 2997 marketed by Cobe Laboratories, and the CS3000 marketed by Fenwal Laboratories operate by these means. These systems, however, are expensive and complicated to run. Because plasma has a density of 1.0269 and platelets have a density of 1.03 (red blood cells have a density of 1.10), the difficulty of fractionation has heretofore precluded the usage of substantially simpler and less costly systems. Thus manual plateletpheresis, which has been in use for more than 25 years, is still employed. Here a batch type two-step centrifugation process operating on single units of blood is used with a first lower velocity spin to derive platelet rich plasma, and then with a second higher velocity spin to concentrate the platelets. This not only requires much manual handling, but supplies from separate donors must be mixed in order to obtain an adequate amount of platelets for platelet transfusion.

Human blood normally is composed of about 50% plasma and much less than 1% of platelets in a concentration of approximately 250,000 platelets per microliter of whole blood. Thus when plasma is separated from the blood together with substantially all platelets there will be 500,000 to 550,000 platelets per microliter of plasma (the "Norm"). Platelet concentrate is usually regarded as having approximately 1.1 million platelets, or more, per microliter of plasma. Obtaining plasma that is platelet rich above the norm as well as free of hemolysis, and doing so on a continuous basis compatible with donor flow rates (typically about 50 ml/min) is therefore a most worthy objective. Red blood cells and some plasma can concurrently be returned to the donor as the platelet rich plasma is stored or otherwise made available for platelet transfusion or other purposes. If a high platelet concentrate (e.g. 4,000,000 platelets/microliter) is desired on a real time basis then an in-line rotary membrane filter can be employed as described in the above-mentioned Schoendorfer et al application.

A one-step procedure for extracting platelet rich plasma from whole blood solves a very difficult problem, and the procedure should moreover be amenable to usage with other applications where it is desired to selectively extract one constituent or target material from both heavier and lighter matter in a suspension.

SUMMARY OF THE INVENTION

Systems and methods in accordance with the invention establish an initially partially or fully stratified flow in a centrifugation zone, but then introduce localized remixing propagated from the opposite direction. The localized remixing regions are controlled and predictable in position in the centrifugation zone and provide the basis for improved separation of constituents. Remixing is generated by interactions established between fluid in an internal centrifugation zone within a double-walled rotor, and an outer differentially moving recirculation zone that encompasses the centrifugation zone. If blood is the fluid suspension being separated, platelet rich plasma is extracted inwardly through ports adjacent the localized remixing regions while heavier and lighter constituents move radially outward through blood outlet ports in the rotor. The system is biologically closed, and with whole blood as the input obtains plasma that is rich in platelets above the norm while returning platelet-depleted blood flow to a donor.

A feature of the invention is that, in the continuous extraction of matter, flow rates can be adjusted to vary the constituents making up the lower density output from the device. The separation of at least partially stratified material within the centrifugation zone therefore appears to take place at regions that are closer to or further from a transition zone between light and heavier density material. Consequently, with blood as the medium being separated, outputs can be derived, solely by adjusting flow rates, that maximize platelet rich plasma or provide more pure plasma on the one hand or blood cell constituents on the other.

Another feature of the invention resides in the use of internal pumping within the centrifugation zone, and internal recirculation of partially separated matter back to the centrifugation zone so that there is increased use of the separation process even as separated matter is being extracted at different ports.

In a particular example, the rotor structure comprises a double wall body defining a centrifugation gap and rotating within a housing that is spaced apart by the small gap which is used for recirculation. A number of apertures in the outer wall of the rotor generate non-traumatic, localized convective patterns or trailing wakes in the comparatively stationary whole blood confined in the recirculation gap. These patterns trail the apertures in generally circumferential direction, and generate dynamic forces which are propagated through the apertures in the outer wall, and then into the stratified or layered material in the centrifugation zone between the rotor walls. In the centrifugation zone, however, the localized remixing patterns are not circumferential but substantially axial along the rotor, and they furthermore propagate against the principal flow direction. This backward propagation is limited in length by a narrow damping gap in the initial region of the rotor, before the centrifugation zone. It is not fully understood at this time, because of the difficulty of observing small internal flow patterns within the rotor structure, whether a heavier outer stratum or layer is internally mixed so as to improve platelet availability, whether a lighter inner layer is mixed such that a platelet rich shell or surface effect is achieved, or whether some other explanation is appropriate. Nonetheless, it is proven that an unexpectedly high platelet count/unit volume is attained without red blood cells, white blood cells, or hemolysis in the platelet output.

In accordance with other useful features of the invention, the flowing mass is pumped between input and output. Substantial pumping forces are generated by having the blood outlet apertures at a greater radius, relative to the central axis, than the blood inlet apertures. Also, the spacing between the double walls of the rotor is not uniform but defines, from an inlet at one end, first the narrow gap damping zone, then a wider centrifugation gap whose outer boundary increases in radius as matter moves from the inlet to the outlet end, and then a convergent remixing and outlet zone. The divergence of the centrifugation gap provides a differential pressure or pumping action between inlet and outlet.

The recirculation gap is of much higher flow impedance than the centrifugation gap due to its small gap dimension and long length. The recirculation flow is arranged in this example to be of the same order of magnitude as the input flow rate and is very meaningful to throughput and platelet concentration, because by recycling the components of the mass flow it affords greater access of platelets and plasma to the separation dynamics.

Outlet apertures in the outer wall of the rotor lead into the recirculation gap, and thence either into the recirculation path or to the outlet port, while axially aligned concentrate apertures are provided in the inner wall of the rotor, leading through internal conduits in the rotor to a concentrate port along the central axis. The number and size of the ports in the outer wall are related to the number, size, and position of the ports in the inner wall of the rotor, with axial alignment being maintained. The gap and axial displacement of these apertures and ports are also of importance to optimized performance, because the remixing patterns extend across the plasma ports in the inner wall. The radial dimension of the gap along the remixing regions is both tapered and limited in size to minimize hemolysis that could arise from excessive internal circulation.

This system is particularly adapted for real time plateletpheresis applications, in which anticoagulated blood from a donor is fed into a bottom inlet and pumped along a vertically disposed rotor system. One specific example of a plateletpheresis system uses a rotational rate of 2,000 to 3,800 r.p.m., a rotor outer diameter of 1.8", and incorporates a centrifugation gap that starts with a narrow damping gap of 0.005" at the bottom region. The core is narrowed and the shell wall is tapered outwardly so that along its the principal length the centrifugation gap varies from about 0.125" to 0.145", while the gap between the rotor and housing has a dimension of approximately 0.006". With blood inlet flow at approximately 50 ml/min, there is an internal volume such that average residence time is in excess of 30 seconds. With this configuration, blood outlet ports of 0.063" wide by 0.063" high in the outer wall are approximately 30° apart, there being twelve apertures in all. A like number of platelet concentrate outlet ports in the inner wall of the rotor are axially aligned but displaced by 0.465" and are 0.035" wide by 0.075" high in size. The degree of taper, the internal blood confinement volume, the sizes and the relative positions of the apertures all are utilized to achieve a superior combination of flow rate and efficiency. Total flow rate for a specific purpose or general application may be varied by applying a suitable form factor to dimensions and volumes, while maintaining the gaps approximately the same size.

BRIEF DESCRIPTION OF THE DRAWINGS

A better understanding of the invention may be had by reference to the following description, taken in conjunction with the accompanying drawings, in which:

FIG. 5 is a perspective fragmentary view, partially broken away, of a portion of the outlet end of the separator of FIG. 1;

DETAILED DESCRIPTION OF THE INVENTION

The system and device of FIGS. 1-7, to which reference is now made, confront the many difficulties presented by the objective of extracting platelet concentrate directly from whole blood. This is only one example of the problem of obtaining a concentration of an intermediate density or target constituent from both heavier and lighter constituents in a homogeneous flow. Unusually severe problems resident in this objective as applied to plateletpheresis arise from such factors as the viscous character of blood, the fragile nature of its cellular constituents, the very low percentage of platelets in whole blood, the low density differential between the plasma, platelets, red blood cells and white blood cells, and the desirability of return of all useful blood constituents to the donor substantially concurrently with the separation, and within a reasonable time. There is also a need to perform these functions with a low cost, disposable, easily installed, simply operable, and biologically closed device that is efficient despite variations in blood from different donors. All these desiderata are met by devices and systems in accordance with the invention.

Figure 1:
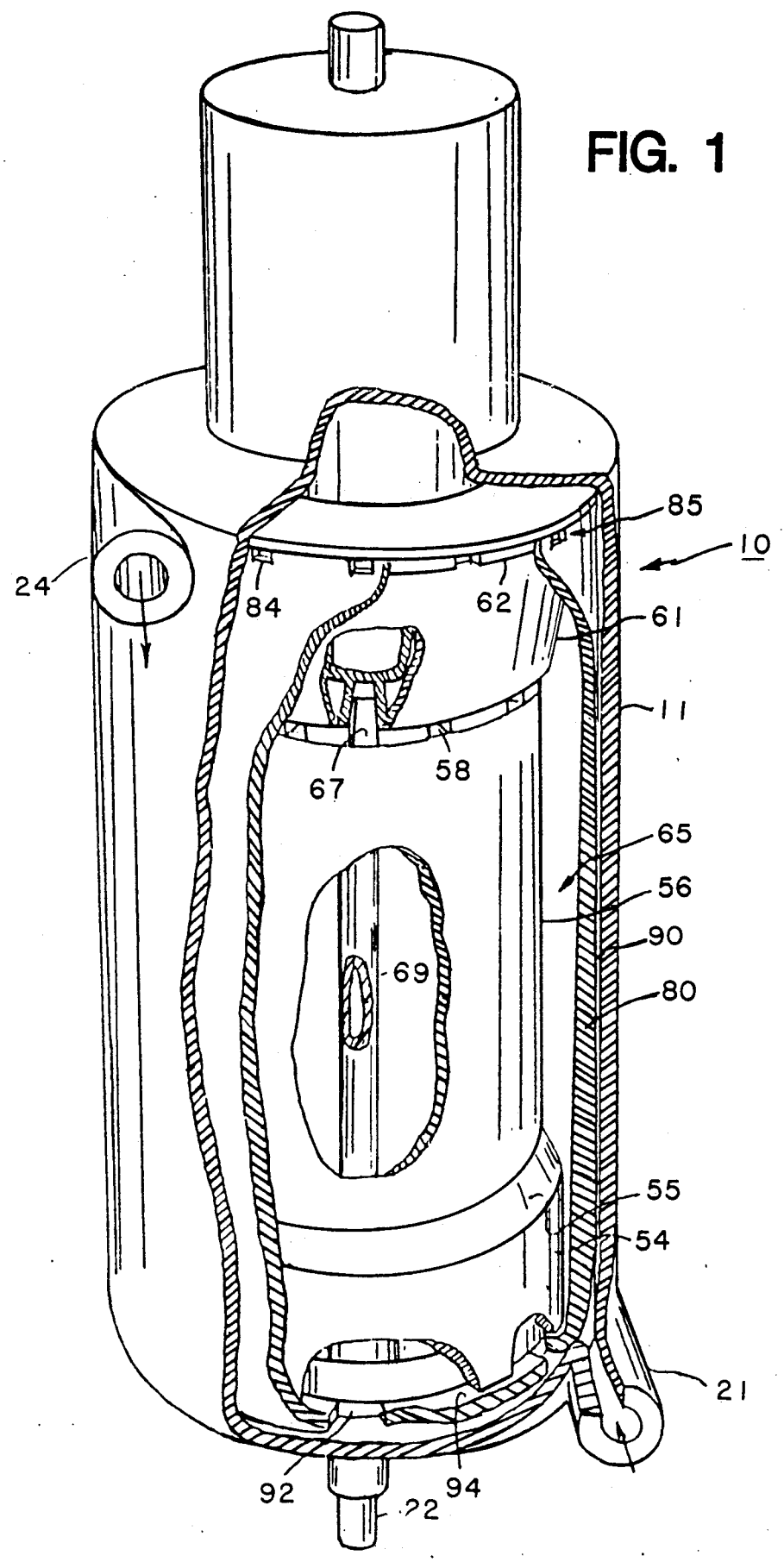
FIG. 1 is a perspective view, partially broken away, of a disposable platelet separator.
Figure 2:
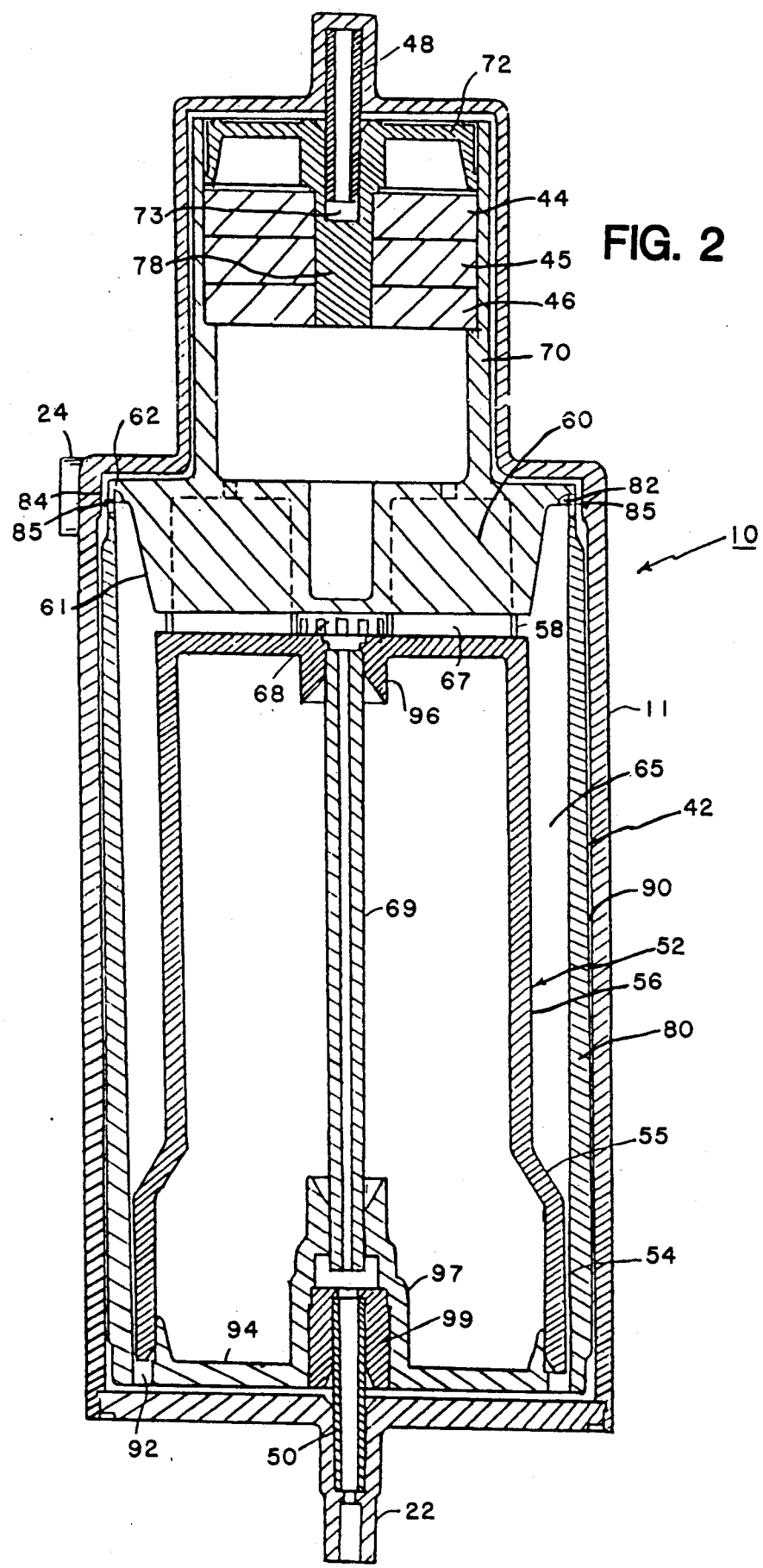
FIG. 2 is a side sectional view of the separator of FIG. 1.
Figure 3:
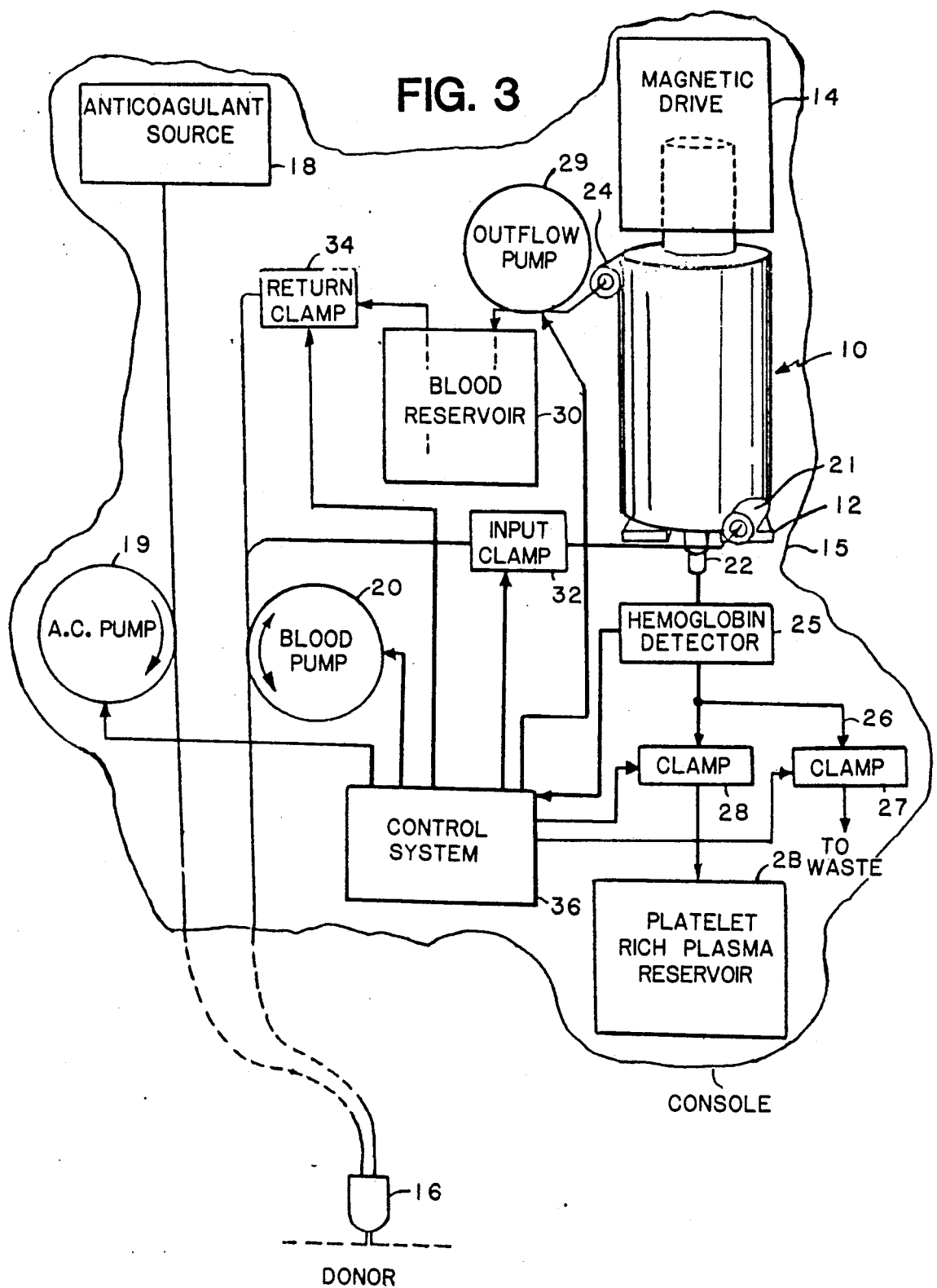
FIG. 3 is a combined block diagram and simplified perspective view of a system for plateletpheresis in accordance with the invention.

The disposable separator device 10 is depicted in the various views of FIGS. 1, 2 and 4-7, while the principal elements of a complete separator system are shown in FIG. 3. To establish the context and specific application, the system will be described first, in general terms.

Referring to FIG. 3, the blood separator device 10 has a housing 11 that is insertable between a bottom holder 12 and a spaced apart magnetic drive 14 mounted on a console panel 15. The magnetic drive device 14 receives the upper end of the separator 10 and rotates its interior mechanism by coupling a rotating magnetic field to an internal magnetic element, as described in detail below. Whole blood derived from a donor by a single needle 16 (a double-needle system may alternatively be used) is anticoagulated by anticoagulant from source 18 through a pump 19. This pump and other pumps in the system are preferably of the peristaltic type. The anticoagulated blood is then pumped by a reversible blood pump 20 into an inlet of the separator 10 to establish a pressure of about 380-400 mm Hg to overcome gravity and pressure drops in the device. The rotating separator device 10 receives the blood at a lower tangential inlet 21 to the housing 11 and passes platelet rich plasma out via a coaxial outlet 22, while platelet depleted blood exits at an upper tangential outlet 24. The platelet rich plasma is at approximately ambient pressure and is passed by gravity through a flexible tubing downwardly to a platelet reservoir 23. In this path the outflowing platelet rich plasma passes a hemoglobin detector 25 and a flexible shunt line 26. Each of the shunt line 26 and the outflow tubing can be selectively closed by a signal responsive clamp 27 or 28 respectively. The blood output from the outlet 24 is at high positive pressure (300-400 mm Hg typically) and fed into one side of a reservoir 30, via a controllable pump 29 which normally provides only enough differential output pressure to the reservoir (about 10-20 mm Hg) to maintain a constant selected flow rate. From the blood reservoir 30, platelet poor blood is transferred by the blood pump 20 to the single needle 16 in timed phases separate from the withdrawal phases.

Maintaining a positive pressure on the blood is not theoretically necessary inasmuch as differential pressures establish the flow rates and the platelet enriched plasma could be pumped out under negative pressure. As a practical matter, however, substantial negative pressure can cause vaporization to commence, and this is best avoided.

Because single needle operation is generally preferred for donor comfort, blood is withdrawn and returned in alternate phases, the reservoir 30 serving as a buffer for this purpose. With a reservoir of sufficient size there need be only one complete cycle, although generally several cycles will be used to limit the total amount of whole blood removed from the donor at any one time. To enable a single blood pump 20 to be used, signal operated clamps 32 and 34 in the input and return lines respectively are used to open and close these conduits.

Any of a variety of other system configurations can be employed. For example with a single needle a dual chamber reservoir could be used and platelet depleted blood pumped from the first reservoir to the second at a constant rate.

A conventional form of control system 36 is coupled to the various pump sensors and clamps in the system, to sense conditions of operation and to govern flow rates, paths and durations, as well as to provide steady state and alarm displays. Inasmuch as these functions are currently being performed on a number of known hemapheresis systems that withdraw blood from and reinfuse it into a donor, most of them are not shown or described in detail in the interests of simplicity and brevity. Manual control of the various devices is feasible but not preferred for general use. Disposable tubing is used to transfer fluids within this system; along with disposable reservoirs 28, 30 and the disposable separator 10, so that no cross-contamination between patients can result. The clamps 32 and 34 in the lines to the needle 16 are operated by the control system 36, as are the clamps 27, 28 in the platelet rich plasma outflow line. When in excess of a predetermined level of hemoglobin is sensed in the outflow line by the detector 25, the shunt line 26 is opened by releasing the clamp 27 and the main line is closed by the clamp 28. Flow conditions can then be adjusted until platelet rich plasma is again flowing, at which an operator or the control system 36 resets the clamps 27, 28. The control system 36 also governs pump 20 direction, to return blood from the blood reservoir 30 for reinfusion in the donor via the needle 16. To reinfuse platelet depleted blood in the donor the pump 20 is rotated in the proper direction and the return line clamp 34 is opened while the input line clamp 32 is closed. This action is carried out after a sufficient quantity of platelet rich plasma concentrate has been accumulated or when the reservoir 23 contents reach a predetermined level or mass. Devices for detecting the amount in the blood reservoir 30 and in the platelet rich plasma reservoir 23 have been omitted for simplicity.

The separator 10, which is shown in detail in FIGS. 1, 2, and 4–7, to which reference is now specifically made, supports the cylindrical housing 11 on a generally vertical axis. Thus the whole blood inlet port 21 in the housing 11 is positioned tangentially proximate the housing lower end, as it supplies input blood from the donor. An internal double walled rotor 42 is rotatably disposed within the housing 11, concentric with the central axis of the separator 10, which is typically vertical. A group of magnetic elements 44, 45, 46 is disposed in and coupled to the upper end of the rotor 42, and positioned within the magnetic drive device 14, when the separator 10 is mounted in operative position. A rotating magnetic field within the drive device 14 couples to the rotor to establish a desired rotational rate, in the range of 2,000 to 3,800 r.p.m., and here 3,600 r.p.m. The opposite ends of the rotor 42 engage low friction supports comprising an upper pivot pin 48 and a lower, hollow pivot pin 50 seated in opposite ends of the housing 11 (see FIG. 2 particularly). Adjacent the upper end of the housing 11, the tangential blood outlet port 24 provides platelet depleted blood through the pump 26 to the blood reservoir 30, while the coaxial platelet concentrate outlet 22 at the bottom of the housing 11 feeds matter passing through the central bore in the lower pivot pin 50 by gravity flow into the platelet reservoir 23. Referring also to the details shown in FIGS. 4–5, the internal construction of the separator 10 is of significant importance to the functions being performed. The double walled rotor 42 spans the axial length between the blood input and output ports 21, 24 respectively and in this region is of generally cylindrical outer form. It includes an inner cylindrical wall or core 52 of a varying profile that has a substantially continuous surface except for circumferentially disposed platelet concentrate ports 58 near its upper end. At its lower end, the rotor core 52 has a straight damping wall 54 section of 1.634" diameter and 0.25" length, adjacent an inwardly tapered length 55 leading to a straight principal wall section 56 of 1.390" diameter and 3.560" length. Twelve evenly spaced platelet rich plasma ports 58 of rectangular shape, being 0.035" wide by 0.075" high, lead radially inwardly at the top of the wall 56. At an upper section 60 of the core 52, above the ports 58, the rotor core 52 includes an outwardly tapered or divergent wall 61 leading to a peripheral lip 62. This divergent wall 61 and the straight wall 56 below it define a centrifugation zone 65 within the outer wall of the rotor 42.

Advantageously for low cost molding purposes, the rotor core 52 is made in two pieces joined at the plane intersecting the lower edge of the platelet concentrate ports 58. This upper section 60 is most clearly seen in the views of FIGS. 6 and 7.

Figure 6:
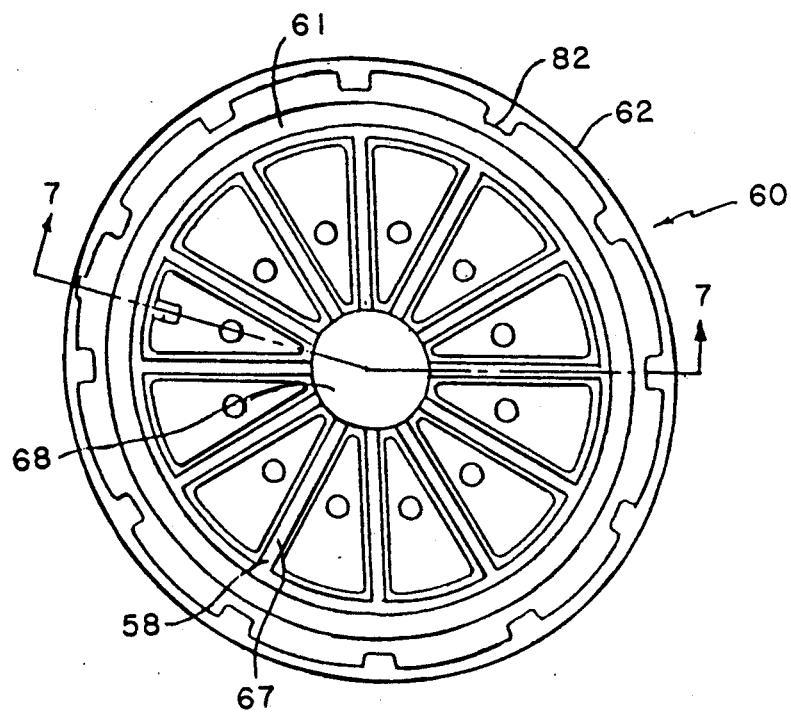
FIG. 6 is a bottom view of the upper portion of the rotor core structure.

As best seen in the views of FIGS. 2 and 6, the separate top section 60 includes radial passageways 67 leading inwardly from the platelet concentrate ports 58 into a central manifold region 68 that communicates via a central hollow tube 69 with the coaxial platelet concentrate outlet 22 via the hollow lower pivot pin 50. The top section 60 of the rotor core 52 includes a wall 70 of smaller diameter, fitting closely within a reduced diameter top of the housing 11 and including vertical internal projections 71 for receiving the somewhat star-shaped magnetic elements 44–46 in mating relation. The top section 60 is closed off by an end cap 72 that includes a coaxial recess 73 for retaining the lower end of the upper pivot pin 48. The end cap 72 also includes a downwardly projecting central mandrel 78 that engages within central apertures in the magnetic elements 44–46.

An outer wall or shell 80 of the double walled rotor 42 is of 1.799" outer diameter, is joined to the peripheral lip 62 in the core top section 60 and is concentric with the central axis. The inner surface of the shell 80, however, is tapered to provide a constant outwardly diverging aspect in the centrifugation gap 65 (in the upward flow direction) with respect to the straight section 56 of the core 52. In this example, the space between the damping wall 54 of the core 52 and the inner wall of the shell 80 is 0.0005". The spacing then diverges (at an angle of about 0.5°) in the centrifugation zone 65, to expand the minimum gap, of approximately 0.125" immediately above the tapered section 55, to approximately 0.145" at the upper end opposite the platelet concentrate ports 58, along a length of about 2.09". The outward taper of the top section 60 of the rotor core 52 again diminishes the gap as the peripheral lip 62 is approached in the upward direction. The radial dimension of the gap above the ports 58 is reduced in size by the converging section, to limit internal circulatory movements in the blood and tendency to hemolysis in this region. Also, any bubbles in the blood move upwardly within the flow, and also inwardly, so that they leave the system via the platelet concentrate ports 58.

Symmetrically disposed notches 82 in the underside of the lip 62 (FIGS. 2, 6 and 7) are facing and adjacent notches 84 (FIGS. 1 and 2) in the top edge of the shell 80, to provide blood outlet ports 85 for blood flowing from the gap 65 between the rotor core 52 and shell 80. The outer surface of the shell 80 is separated from the inner surface of the housing 11 by a flow or recirculation gap 90, which is here 0.006" along the majority of its length. However, this recirculation flow gap 90 is made slightly greater at the bottom and top of the shell 80 by reducing the outer diameter of the shell 80 at its axial ends to accommodate inlet and outlet flows at the lower and upper ends, respectively.

The space between the rotor core 52 and shell 80 is in communication with a series of six equally spaced apart blood inlet ports 92 (0.228" by 0.062") in a bottom wall 94 of the shell 80. These inlet ports 92 are at 0.785" radius from the central axis, whereas the blood outlet ports are at 0.889" radius. The difference in radii results in substantially greater velocity at the output ports, providing a substantial pumping force in the upward direction on the blood. Most of the blood passing through the blood outlet ports 85 enters the recirculation path and is relatively quickly pumped down to the bottom end to reenter the inlet ports 92. In this example, relative port sizes and internal volume (about 30 ml) provide a recirculation flow that is about equal to the input flow, and an average residence time of the order of 20 seconds. Specifically the average residence time of blood in this exemplary separator 10 is determined by the ratio of internal volume, 30 ml, to input flow rate (50 ml/min) plus the recirculation flow rate (50 ml/min), or 18 seconds.

The driving force available for pumping blood from the outlet (upper) end back to the inlet (lower) end of the device 10 is the differential pressure ($\Delta P$ or $P_2 - P_1$) exerted because the flow apertures are at different radii, with $R_o$ (output) being at about 1.75" (2.225 cm) and $R_i$ (input) being at about 1.1633" (2.074 cm). The relationship between rotation and resulting pressures as a function of radius can be shown to be:

$$\tfrac{1}{2}\rho\omega^2(R_o^2 - R_i^2) = P_2 - P_1,$$

where $\rho$ = density, here about 1.06 for blood of intermediate hematocrit between low (1.04) input hematocrit and high (1.09) output hematocrit
and
$\omega$ = 377 rad/sec based on a 3600 r.p.m. rotation With these values, a $\Delta P$ ($P_2-P_1$) of 48087.6 dyne/cm$^2$ is derived, this converting to 0.7 psi or 36 mm Hg. To compute the theoretical mass flow per unit time, W, one can use the formula relating to pressure drop in an annular duct given at page 5-25 of Perry, *Chemical Engineer's Handbook*, 5th Edition, McGraw Hill Book Company, New York (1973), specifically $$W = \frac{-(D_2^2 - D_1^2)N}{128}\left[D_2^2 - D_1^2 - \frac{D_2^2 - D_1^2}{2.3\log_{10}}\left(\frac{D_2}{D_1}\right)\right]$$

where $N = \frac{\rho G_c}{\omega}\left[\frac{\Delta P}{L}\right]$ $D_2 = 1.800''$ (0.15')
$D_1 = 1.783''$ (0.1486')
$G_c = 32.17$ (dimensional constant)
$L = 3.25''$ (0.27')
$\omega = 0.04$ poise ($2.69 \times 10^{-3}$ lb/ft.sec)

This yields a mass flow rate W of $1.054 \times 10^{-3}$ lb/sec, or about 32 ml/min as a theoretical value. However, actual recirculation flow rates are strongly influenced by volumetric relationships and the dimensions of the input and output ports. The order of magnitude of the flow rate was verified by measuring pressure drop through the annular gap between a rotor and housing having like dimensions to those given above, but with no centrifugation gap in the rotor. Both saline and 40 hematocrit blood were run, and it was found that for a flow of 100 ml/min there was a 72 mm Hg pressure drop for saline at both 0 and 3,600 r.p.m. The same flow rate for blood gave a measured pressure drop of 75 mm Hg. Using these relationships together with the $\Delta P$ of 36 mm Hg as calculated above, the recirculation flow rate in the device is about 50-60 ml/min. This is of the same order of magnitude as the calculated value given above. Thus in the present example, in which blood is inputted at about 50 ml/min and platelet-poor blood is removed at 38 ml/min, the net recirculation rate is about 50 ml/min and the flow through the centrifugation gap is about 100 ml/min. Consequently an increment of blood is processed approximately twice in the centrifugation zone before leaving the device.

With blood as the circulating medium, there is an added limitation because, as noted below, too small a recirculation gap induces hemolysis in the blood. However, it is clear that the added centrifugation time, and perhaps the increased hematocrit of the platelet and plasma depleted blood being recirculated, contribute significantly to the efficiency of platelet separation. The recirculation function is characterized by the fact that both the pumping sources and the return flows are internal to the housing, and also by the fact that output flows are constantly extracted after a condition of stability is reached.

Whole blood introduced tangentially into the volume between the housing 11 and rotor 42 thus finds a preferential path into the centrifugation zone 65 via the space between the bottom wall 94 of the rotor shell 80 and the housing 11 bottom wall, then through the blood inlet ports 92 and the gap between the turbulence damping wall 55 of the core 52 and the shell 80. The preferred upward path is substantially all within the rotor 42 because of the pumping effect and because the flow impedance presented by the long recirculation gap 90 is much greater than that of the centrifugation gap 65. The further pumping action provided by the divergence in the centrifugation gap 65 also aids in establishing this flow.

At the upper end, the blood outlet 24 from the housing 11 is in the same horizontal plane as the blood output ports 85 in the shell of the rotor 42. The blood outlet ports 85 in the rotor 42 are in a horizontal plane separated by 0.465'' from the horizontal plane of the platelet concentrate ports 58. The blood outlet ports 85 are equal in number (twelve) and are at like circumferential positions, 30° apart, relative to the platelet concentrate ports 58. Each of the blood outlet ports 85 has dimensions of 0.063'' wide by 0.063'' high in this example.

As best seen in FIG. 2, the top wall of the lower rotor core 52 section includes a downwardly directed central hub 96, while the shell bottom wall 94 includes an upwardly directed central hub 97. The central hollow tube 69 is seated at its opposite ends in central openings in these two hubs 96, 97. The lower hub 97 also is configured to receive a bearing 99 which engages the lower hollow pivot pin 50 at an internal shoulder and supports the weight of the rotor 42.

In operation, this system processes a fresh anticoagulated blood flow of normal hematocrit at approximately 50 ml/min within 50-60 minutes to derive a high volume of platelet rich plasma with significant improvements over the prior art. Although the product flow rate varies inversely with hematocrit, as is to be expected, in 50-60 minutes of operation, with one vein access, greater than $3 \times 10''$ platelets are derived in 500-600 ml of platelet rich plasma in a typical example. This assures a flow of in excess of 600,000 platelets per microliter and enables virtually any desired concentrate level to be obtained by a further membrane filtration step, with plasma being derived as a byproduct.

These results are achieved in a stable, non-critical mode of operation with minimal hemolysis and white blood cell content in the output. Nevertheless, it should be recognized that the system is based on flow geometries and fluid dynamics which make beneficial use of a complex of interactions to provide an accessible flow of carrier rich in the desired constituent. Conceptually, dimensions and physical relationships can be varied widely for different applications. In any specific application, however, the relative sizes of elements and spacings within the separator and the densities and viscosities of the constituents of the input mass will affect the optimum geometry for achieving a given flow rate, concentration and efficiency. For this reason, various specific dimensions and spacing relationships have been given above for the unique and critical blood application that is described as the specific example.

A device for the extraction of platelet rich plasma from whole blood is constrained by certain inherent requirements that affect design, such as the need to be compatible with donor supply rates. The device should also avoid damage to the fluid system, comprise a single use, low cost, sterile disposable to minimize the chances of cross-contamination, and provide a sterile, closed system. Such factors not only affect the sizes and geometries but also influence the choice of materials that can be used.

With such qualifications in mind it can be said that a principal aspect of the invention involves continuous movement of a centrifuging mass in one direction along and about a centrifuging axis, and propagation within that flow, in the opposite direction, of localized controlled remixing motions which preferentially affect a chosen intermediate density constituent. The separation is aided by recirculation of a major portion of the centrifuging mass and better control of the localized motions is gained by damping the reverse propagation.

Figure 4:
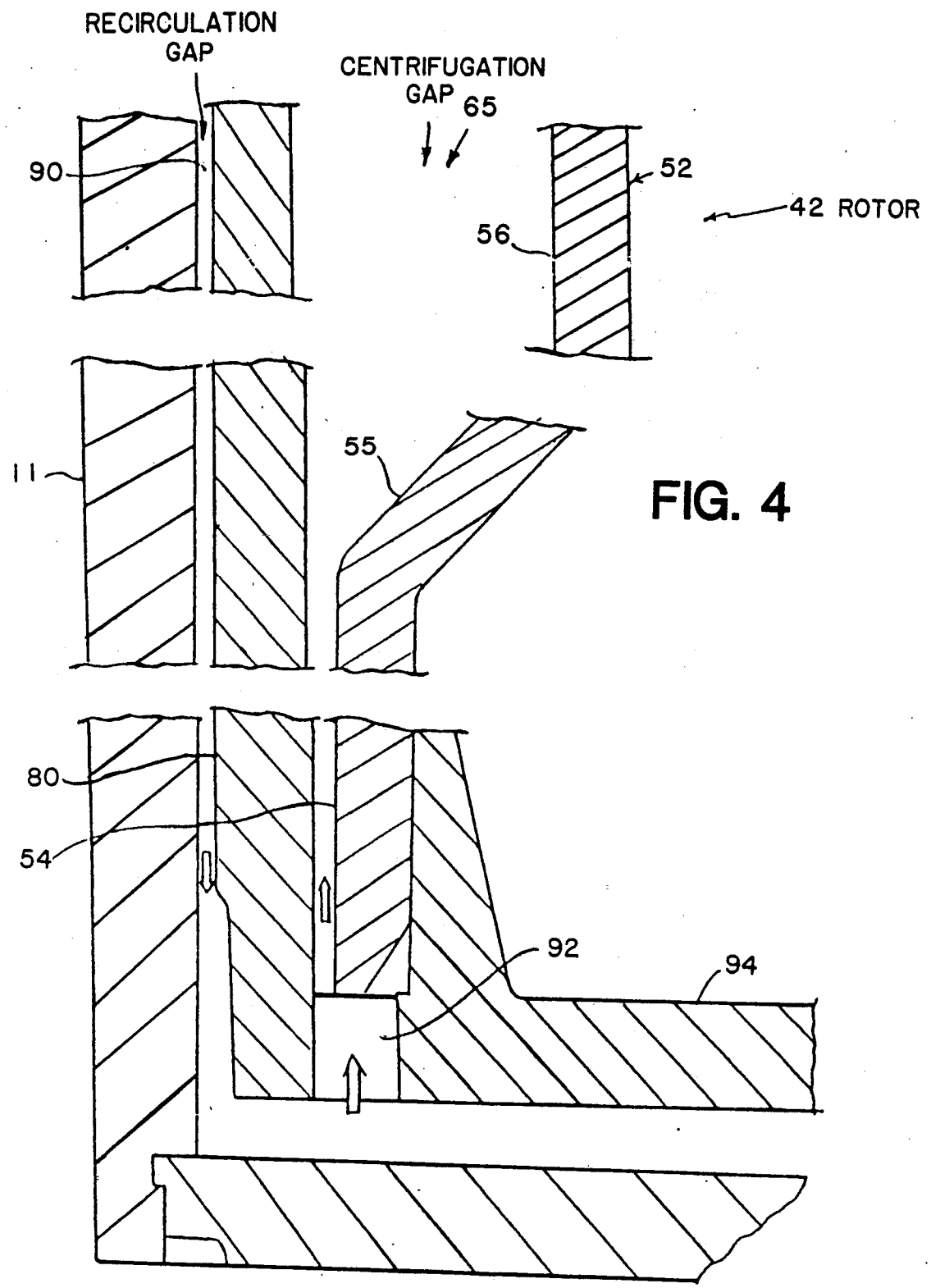
FIG. 4 is an enlarged fragmentary sectional view of a portion of the inlet end of the separator of FIGS. 1 and 2.
Figure 7:
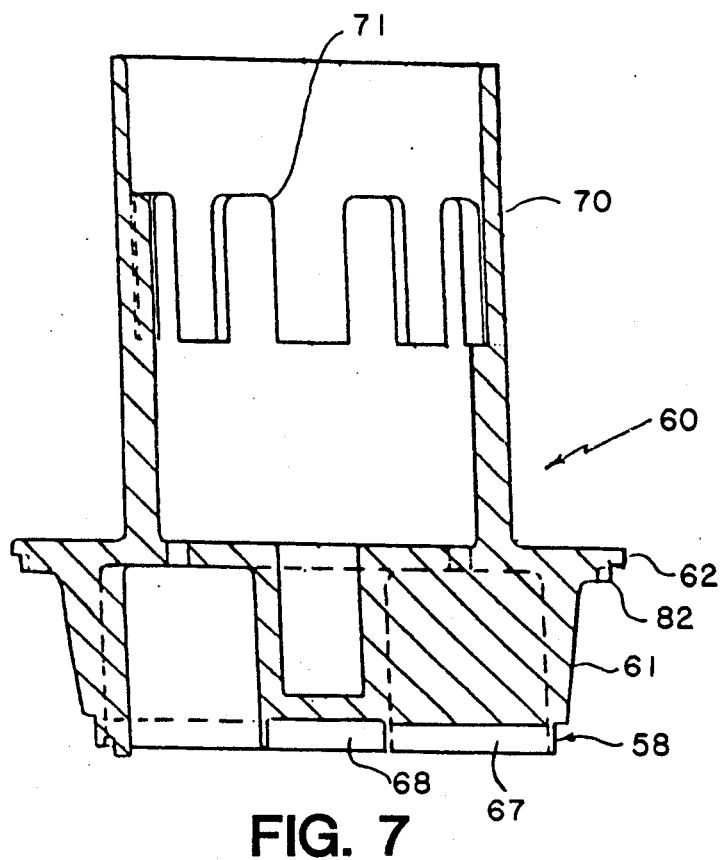
FIG. 7 is a side sectional view of the upper core portion of the rotor, taken along the lines 7—7 in FIG. 6, and looking in the direction of the appended arrows.

In the system, referring now particularly to FIGS. 1, 2 and 4, input blood flow via the blood inlet 21 into the bottom portion of the flow gap 90 between the housing 11 and rotor shell 80 finds the preferential path into the centrifugation gap 65 through the blood inlet ports 92 in the shell bottom wall 94. The flow impedance presented by the relatively long narrow recirculation gap 90 is much greater than that of the path through the centrifugation gap 65 within the rotor 42, even with the narrow but relatively short length turbulence damping region. An upward pumping action is introduced by the difference in radial positions relative to the central axis between the blood inlet ports 92 and blood outlet ports 85. Centrifugal forces on the blood because of the greater radii of the outlet ports 85 than the inlet ports 92 tend to force the blood mass upwardly within the centrifugation gap 65 and downwardly within the recirculation gap 90. Upward pumping is also aided by the constant increase in the expanding centrifugation gap 65, as the blood proceeds axially. When the centrifugation gap 65 is filled, which occurs within a few seconds, flow rates begin to stabilize, and a number of different flow relationships are established, commencing the separation action which fully stabilizes some seconds later.

In steady state operation the rotor 42 is spun at 3600 r.p.m., and the centrifugal force exerted on the blood in the centrifugation gap 65 for a 1.8" outer rotor diameter and a thin shell wall for the rotor 42 is approximately 330 g's. Non-turbulent flow is established in the bottom portion of the centrifugation gap 65 by initial stabilization within the narrow gap along the turbulence damping wall 54. Relatively non-turbulent flow exists along the principal portion of the centrifugation gap 65, along the length of the straight wall 56 and upper divergent wall 61 of the rotor core 52. By "relatively non-turbulent flow" is meant that stratification or layering occurs but that the dynamics of operation involve other motions as well, which however are non-traumatic to the blood. The flow reaches full steady state after the centrifugation gap 65 and platelet concentrate ports 58 are filled and blood moves outwardly through the blood outlet ports 85 in the shell 80 to fill the recirculation gap 90, passing downwardly to the bottom within the housing and remixing with inlet whole blood. Steady state flow also involves outflow of a certain fraction of platelet and plasma depleted blood from the upper blood outlet 24, as platelet rich plasma is directed through the platelet concentrate ports 58 in the rotor core 52 to the central region and to the coaxial outlet 22. The average residence time in the separator 10 of approximately 20 seconds, and the downward recirculation flow is estimated to be approximately equal to the input flow to the separator. The typical increment of blood mass recycles at least once through the separator 10 and thus has extended access to the separation dynamics within the device. A substantial level of recirculation is used, although indications from test runs are that more than 500% would be excessive for blood. When visible bubbles are entrained in the recirculating means they can be seen to return to the bottom of the device very rapidly, thus verifying that a major portion of the blood mass is recirculated. The blood in the gap 65 is constantly being mixed because small Taylor vortices are generated in this space.

The preferential platelet separation arises because of effects and relationships in the upper region of the rotor 42. Relative motion between the blood outlet ports 85 in the shell 80 and the encompassing moving blood in the recirculation gap 90 induces a number of localized wakes or secondary patterns as the edge discontinuities at the apertures 85 interact with the circumferentially decelerating blood that surrounds the rotor 42. Reference should be made here specifically to FIG. 5. These localized wakes in the recirculation gap 90 trail each port 85 circumferentially as the rotor 42 turns. Such secondary patterns are believed to be circulatory in nature, but are nontraumatic and nondestructive to the blood. Although they are very difficult to study because of the narrow gap, the placement and strength may well establish Taylor vortices having diameters corresponding to the gap spacing. The localized waves or circulations are depicted only as generalized motion patterns in FIG. 5.

Importantly, the dynamic forces of these outer trailing wakes also induce systematic remixing, perhaps circulatory, effects within the centrifugation gap 65 by transmitting pressure and motion fluctuations back through the blood outlet ports 85. Within the centrifugation gap 65, a number of such localized remixing patterns are propagated axially downwardly, opposite the relatively non-turbulent upward flow of blood in the centrifugation gap 65. The total length of these disrupting patterns is shown in FIG. 5 as extending past the plasma concentrate ports 58. Operative results and studies with visible media, both during operation and by inspection of depositions after shutdown and disassembly, show that the axial circulatory patterns extend at least this far. Sometimes they can propagate downwardly throughout almost all of the centrifugation gap 65. However, the initial turbulence damping region defined by the narrow gap opposite the wall 54 opposes and limits the total length of axial propagation.

Consequently, the centrifugal separation and stratification of plasma, platelets and red cells taking place in the principal flow region of the centrifugation gap 65 is systematically devolved in localized sectors into other flow patterns. Partially or fully stratified layers of plasma and cellular matter are established by the time the upwardly moving centrifuging mass passes the platelet concentrate ports 58. Matter in the zone of stratification is however locally remixed along the circumferentially separated, axially extending, regions by the dynamic forces propagated backwardly relative to the upward motion of the centrifuging mass. This action is such that plasma enriched in platelets is presented at the ports 58 in the rotor core 52. Although the axial remixing patterns are unbounded and not physically restrained by structure in the circumferential direction, they nonetheless are stable.

The preferential separation is meaningfully improved by the recirculation of blood from within the centrifugation gap 65 back downward through the recirculation gap 90. Thus most of the blood mass is in the centrifugation gap 65, and the internal flow has a significantly higher mass flow rate than the relatively equalized output flows. The instantaneous spatial patterns distributed within the centrifugation gap 65 are represented only in conjectural form in FIG. 5 and their establishment and maintenance are discussed further below.

It must be recognized that the patterns in the centrifugation gap 65 are not readily analyzed. The results of the separation process, however, are given here to emphasize the effectiveness of the system. An input flow of 50 ml/min generates a platelet concentrate flow at the platelet concentrate ports 58 and thence the output 22, of about 9-12 ml/min. This platelet concentrate has about 600,000 platelets/microliter or more, with substantially no hemolysis, and with the plasma carrier being essentially free of white blood cells. The platelet depleted blood exits the blood outlet 24 at the differential rate of about 38-41 ml/min. Thus platelet depleted blood sent to the reservoir 30 can be returned in due time via the second pump 20 to the donor. There is no contamination from external sources because all the outlet ports are fixed and no rotating seals are open to the environment.

Platelet rich plasma with platelet concentrations in the range of 500,000 per microliter are routinely generated in batch spinning processes in accordance with the prior art. These, however, have the operative deficiencies mentioned earlier. There is no known technology apart from the previously mentioned Schoendorfer et al application, however, for generation of platelet concentrations higher than this in a continuous flow mode without using further means for separating platelets from plasma.

Applicants have undertaken studies, in the course of analyzing the complex flow patterns within the separator 10, to determine the most significant geometries and relationships. The existence of localized patterns of convection, vorticity or remixing, both outside and inside the centrifugation gap 65, is verifiable to a limited extent through a transparent housing 11 viewed under stroboscopic light synchronized to the rotation of the rotor 42. The presence, position, and to some degree the character, of the localized convective patterns has been made more clear by using flow visualization aids (visible particle matter in suspension) of commercially available types. When such fluid concoctions are run through the separator 10, deposits form on the inside of the housing 11 and on surfaces of the rotor 42 where the flow has been dominated by centrifugal force over turbulence. The residual patterns observed with the present example are on the inner surfaces of the rotor shell 80. The patterns observed show generally axial (i.e. vertical) movement in alignment with the individual blood output ports 85 in the shell 80 and the platelet concentrate ports 58 in the core 52. There is slight waviness along the vertical direction but the secondary patterns pass the platelet concentrate ports 58 in proximate relation.

The existence of such convective patterns and secondary motions are confirmed by video tape recordings made under strobe light illumination through a transparent housing 11 when suspensions with visual aid particulates are in the separator 10. The patterns propagated backwardly (i.e. downwardly) in the centrifuging mass are axial, although some time-varying waviness exists. In the example shown they terminate before the halfway region of the centrifugation zone 65.

As seen in FIG. 5, therefore, one can conjecture that an elongated convective vortex or swirl pattern extends in the centrifugation gap 65 between each of the blood outlet ports 85 and the linearly aligned platelet concentrate port 58. The dynamic remixing action occurring in each such pattern is consistent but complex. In the 0.465" axial separation between aligned pairs of these ports, the induced circulatory or swirl motion, from stroboscopic examinations and deposited visual aid patterns, is axial and quite narrow. Then the circulatory motion may spread somewhat and divert to a more circumferential direction, probably from the mass upward movement of blood between inlet and outlet. It is observed with some test units that the localized circulatory convective patterns can continue down, although diminishing, for some distance (about two-thirds of the rotor length) against the relatively non-turbulent flow.

There apparently is a platelet concentration gradient through each of these localized remixing patterns. The platelet concentration is thought to reflect density differences primarily, but also to be affected by the size and shape of the various blood constituents. Platelets, for example, differ from plasma only slightly in density but because of their size have substantially different drag and acceleration factors in response to the localized circulatory motions from both plasma and other blood cells. Forces acting radially outward in the localized patterns near the platelet concentrate ports 58 may tend to further differentiate platelets from all other cells based on size and/or drag profile. In accordance with this hypothesis, the forces on cellular matter would be greatest near the inner surface of the shell 80 and diminish closer to the inner cylindrical wall 56, thus acting to separate platelets from heavier red and white cells. With the motions and gaps properly disposed, platelets may be thought to be preferentially concentrated in plasma near the ports 58.

Alternatively, it may be that the localized movement within the centrifugation gap 65 acts on the heavier cellular matter at the outside wall, after centrifugation has created some layering. It may then circulate and stir the cellular matter, replenishing platelets in the radially inner layer of plasma, as constituents are withdrawn from the platelet concentrate ports 58. Resupply of platelets and plasma would also be aided by the recirculating flow. In either event, the high platelet concentration results from radially outward passage of both some lighter density plasma and heavier density cellular matter, an effect which is totally unexpected.

The presence of a distinct, if not discrete, transition between stratified cellular matter and platelet rich plasma is confirmed by the use of operative variables, such as pump rates, to vary outtake of plasma, platelets and cellular constituents. By initially maintaining the blood outlet pump 29 at a rate equal to the input pump 20 there is essentially only a straight through flow from the centrifugation gap 65. Slowing down the outlet pump 29 relative to the input pump 20 enables a differential flow to exit via the plasma output ports 58. The extent of this differential needed for high platelet extraction varies with different donors, principally because of differences in hematocrit. However, by setting the differential flow rate so that it is at or close to a maximum *without* hemoglobin being present in the flow, superior platelet counts are derived. One can interpret this in terms of the stratification transition between denser cellular matter at the outer wall of the centrifugation gap 65, and the inner volume in which remixing is occurring. If the inward flow of plasma is too great, hemoglobin is carried in from the outer layer of cellular matter. If the inward flow is too low, plasma is derived with low platelet counts. However with the proper flow an inordinate number of platelets are transported radially inwardly, even though the platelets have slightly higher density than the plasma.

Thus the present system can, solely by balancing flows, vary the constituents in the outflow to emphasize intermediate density material as against both lighter and heavier matter.

A practical example of a sequence of flow variations used in optimizing platelet counts in plasma derived from whole blood is as follows: With the input pump 20 at 50 ml/min the outlet pump 29 is originally set the same, but then slowed down to provide 33 ml/min, giving 17 ml/min out the plasma line, which typically will contain hemoglobin after stable conditions are achieved (there may be an initial reservoir of platelet rich plasma). Then the outlet pump 29 is increased to 40 ml/min, which typically clears up the plasma flow of about 10 ml/min. Then a higher blood outlet flow of say 36 ml/min may be tried to determine if hemoglobin is absent in the plasma, and so on.

A number of factors are of significance with respect to any given configuration of product in obtaining maximum output, without transporting red blood cells into the platelet concentrate. Although the separation process is stable, a short period of time, typically of the order of 60 seconds, ensues before bringing the flow relationships to steady state. Although the average residence time of matter within the above described separator is of the order of 20 seconds, time is required to fill the centrifugation gap 65, then to pump whole blood through the blood outlet ports 85 and through the narrow recirculation gap 90 in the recirculation path to the bottom of the rotor 42. Because of the narrow recirculation gap and the consequent higher flow impedance than in the centrifugation gap, the recirculation volume is only a small proportion of the total flow. However, the recirculation flow rate is approximately equal to that of the input flow rate and is very useful to steady state operation of the separator. Experiments with different numbers and relative spacings of blood outlet apertures have shown that, for this configuration, twelve equally spaced ports 85 of the size indicated provide superior results. Alignment of the platelet concentrate ports 58 axially and with a substantial axial spacing between them, also has been confirmed to approach optimum results. This is consistent with the visualization of the localized vortical flows as proceeding substantially downwardly, in the centrifugation gap, from each blood outlet port 85 to the aligned platelet concentrate port 58.

By changing individual variables over a range, while leaving other variables in the system constant, other relationships significant to achieving maximum efficiency have been identified. Efficiency in this instance reflects the cumulative result, essentially in terms of total platelets derived in a given period of time, thus involving both the platelet concentration and the platelet concentrate flow rate. These two factors often vary in opposite directions, so that selection of the most efficient operating relationships often requires a balancing of the two contributing factors.

A series of runs were made with units in which the degree of divergence of the outer wall relative to the inner wall of the rotor 42 (i.e. the taper of the centrifugation gap 65 in FIG. 2) was varied from 0.035" total to 0.080" total. the platelet concentrate dropped through this range but the output flow rate, $Q_{pc}$, increased at a faster rate. Consequently, the separation efficiency rose because the flow rate was the predominant factor. A taper with a differential spacing of 0.080" was employed in subsequent studies. However, such tests were performed with a 1" rotor and a centrifugation gap of smaller size than with the 1.8" rotor. Although the centrifugation gap was increased and taper decreased in the 1.8" rotor described herein the principle established remains correct, that an optimum taper exists for each set of variables.

In separate studies, the outside diameter of the rotor core 42 was varied relative to the principal part of the tapered length of the outer shell. Small gaps of constant dimension were provided in the lowermost, input region for damping purposes. Thus the average and end limit sizes of the centrifugation gap in the tapered region were changed, which also changed the total volume of blood confined within the centrifugation gap. With the taper having a differential between its limits of 0.080" both the platelet concentrate and the flow rate peaked at about 0.720" core diameter relative to a shell outer diameter of 1.000", giving an average gap of 0.080". Efficiency was maximized in this same region. The characteristic noted was that both the flow rate and the platelet concentrate rate fell off at both ends of the range of gaps. Thus an average gap of about 0.135" was used with a shell having an outer diameter of 1.8".

The depth of the gap between the tapered wall 61 at the upper end of the core 42 and the opposing inner wall of the shell 80 can have an effect on the localized movements within the centrifugation gap 65. Platelet concentrate dropped off somewhat as the gap size was decreased, but the flow rate increased. The optimum efficiency, with assured freedom from entrainment of red blood cells, was found to be with a core top which diverged in the upward direction, providing a convergent end to the centrifugation gap. When the gap was too small then the output through the platelet concentrate ports 58 was essentially only clear plasma. On the other hand, when the gap was too large, then red blood cells tended to be present in the plasma. Too large a gap in this region appears to allow excessive interior motion so that red blood cells appear and hemolysis results. Too small a gap seems to provide no or ineffective mixing within the stratified layers, so that only plasma, the lowest density constituent, tends to appear at the platelet concentrate ports 58. Making the core top diverge in the upward direction also aids in directing all air in the separator to the platelet concentrate ports 58. This greatly simplifies initial priming of the separator.

In the optimal unit shown that was designed for 50 ml/min input flow rate of whole blood, it was found that efficiency was greatest at 50 ml/min input even though higher flow rates can be supported. At higher input flow rates the concentrate flow rate does not change significantly and although the platelet concentrate increases somewhat, the output flow rate predominates and the net result is a decrease in efficiency. In addition, donor flow rates as a practical matter are limited to the 50–60 ml/min range.

Finally, the relationship between the gap between the rotor and the housing and the resulting flow of platelet concentrate is of significance. At the given r.p.m. (3600) and rotor radius noted above hemolysis becomes measurable at recirculation flow gaps below 0.004". As the gap increases above 0.010" the rate of flow of platelet rich plasma decreases. The present hypothesis is that the effect is due to the overpowering nature of the amplitude of the recirculating flow on the separation zone.

It will also be recognized by those skilled in the art that it is readily feasible to operate the system in an inverted relationship, with whole blood input flow being at the top, the taper diverging downwardly, and platelet concentrate ports being adjacent the lower end of the rotor so as to have a shorter flow path to the coaxial output port. Devices of this configuration have been constructed and operated with satisfactory results, but the arrangement shown in FIGS. 1-7 appears to be more quickly stabilized and to provide a somewhat better separation action.

It will be evident that, based on these understandings, preferential separation of many other lighter and intermediate weight constituents within a carrier or liquid suspension is feasible, given adaptation of the principles of the invention to the particular application. Backward propagation of localized internal motions within an advancing centrifuging mass may require more or less initial damping and recirculation flow to provide the desired combination of throughput and efficiency. Viscosities, particle sizes, density differentials and a variety of other factors may have to be considered in evolving an optimal design. However for many uses far higher rotational speeds and flow rates can be employed without danger of traumatic effects to the substances, and the concepts may be utilized in such instances with far fewer constraints than apply to a fragile medium such as whole blood.

While a number of expedients and variations in accordance with the invention have been described, it will be appreciated that the invention is not limited thereto but encompasses all forms and variations within the scope of the appended claims.

What is claimed is:

1. Apparatus for separating platelet rich flow from whole blood comprising:
   a cylindrical housing including means for flowing blood constituents therealong:
   a hollow walled rotor mounted within the housing and rotatable therein about a longitudinal central axis concentric with the housing, the rotor including inner and outer walls defining a diverging centrifugation gap in the direction along the axis, the rotor including input ports adjacent one end thereof for feeding whole blood constituents into the gap;
   means for rotating the rotor at centrifugation speeds to establish internal layering of the blood constituents within a given portion of the rotor spaced from the input ports;
   means within the rotor and coupled into the centrifugation gap between the rotor walls to provide an output flow of platelet rich matter along the central axis of the rotor, said means including platelet concentrate ports in the inner wall of the rotor adjacent an end opposite from the input ports;
   means for extracting platelet poor blood output, said means including apertures in the outer wall of the rotor disposed adjacent but spaced apart from the platelet ports in the direction of the diverging centrifugation gap; and
   means for inducing localized circulation patterns that originate adjacent to said platelet poor blood extracting means into the blood constituents in the centrifugation gap in the region of the platelet concentrate ports.

2. An apparatus according to claim 1 wherein the means for inducing localized circulation patterns comprises the apertures in the outer wall of the rotor and blood in the space between the housing and outer wall of the rotor.

3. An apparatus according to claim 2, wherein the apertures in the outer wall of the rotor are regularly spaced in the circumferential direction about the outer wall of the rotor and the platelet concentrate ports are spaced apart at positions in alignment with said apertures.

4. An apparatus according to claim 3 wherein the space between the rotor inner and outer walls adjacent the platelet concentrate ports on one axial side thereof is larger in size than the centrifugation gap at the other axial side of the platelet concentrate ports and converges from the platelet concentrate ports to the apertures in the outer wall.

5. A centrifugal separator comprising:
   a housing disposed about a central axis, the housing having an inlet for receiving a fluid that is to be separated and an outlet axially spaced from the inlet;
   a double wall rotor having inner and outer walls mounted for rotation about the central axis within the housing with a first gap being defined between inner and outer walls of the rotor and a second gap being defined between the outer wall of the rotor and the housing, the outer wall of the rotor having at least one inlet aperture therethrough at a location closer to the housing inlet than to the housing outlet for passing the fluid that is to be separated from the second gap through the outer wall of the rotor to the first gap, the outer wall of the rotor having at least one outlet aperture therethrough at a location closer to the housing outlet than to the housing inlet for passing a first fraction of the fluid to be separated from the first gap through the outer wall of the rotor to the second gap and to the housing outlet, the rotor having a passageway communicating with a radially inward portion of the first gap for removing a second fraction of the fluid to be separated from the first gap, and the first and second gaps being shaped to provide a flow of fluid through the first gap from the rotor inlet aperture to the rotor outlet aperture and a flow of fluid through the second gap from the rotor outlet aperture to the rotor inlet aperture, the flow of fluid through the second gap being less than the flow of fluid through the first gap.

6. A centrifugal separator according to claim 5 wherein the first gap is shaped to centrifugally force fluid within the first gap from the inlet aperture toward the outlet aperture.

7. A centrifugal separator according to claim 6 further comprising a magnetic drive coupled to impart rotational force to the rotor with no mechanical through the housing.

8. A centrifugal separator according to claim 5 further comprising a flow passage defined along the central axis, the flow passage extending between the rotor and the housing, the flow passage having a seal intercoupling relatively rotating portions of the flow passage defined respectively by the rotor and by the housing and being coupled to receive the second fraction from the passageway and carry the second fraction to the housing.

9. A centrifugal separator comprising:
a housing disposed about a central axis and having an inlet for receiving a fluid that is to be fractionated and an outlet axially spaced from the inlet for passing a fraction of the fluid that is to be fractionated; and
a double wall rotor having inner and outer walls disposed within the housing concentrically about the central axis for rotation about the central axis, the rotor defining a first axially extending gap between the inner and outer walls and a second axially extending gap between the outer wall and the housing, the outer wall of the rotor having an inlet aperture therethrough which is axially located closer to the housing inlet than to the housing outlet, the outer wall of the rotor having an outlet aperture therethrough which is axially located closer to the housing outlet than to the housing inlet, the first and second gaps extending axially between the outer wall inlet and outlet apertures and the second gap extending circumferentially completely around the outer wall of the rotor and including means to direct a flow of fluid in the second gap from the rotor outlet aperture to the rotor inlet aperture.

10. A centrifugal separator according to claim 9 further comprising a magnetic drive disposed to impart rotational force to the rotor without mechanical coupling through the housing.

11. A centrifugal separator according to claim 10 wherein the rotor includes a lighter matter passageway disposed to conduct a fraction of the fluid to be fractionated from a radially inward region of the first gap to a containment volume.

12. A centrifugal separator according to claim 11 wherein the fluid to be separated is centrifugally separated within the first gap with a heavier fraction passing radially outward through the outlet aperture and a lighter fraction passing through the lighter matter passageway.

13. An apparatus for separating from a carrier having constituent parts a preselected constituent comprising:
means for establishing a rotating centrifugal zone,
means for introducing the carrier into said rotating centrifugation zone in a direction generally parallel to the axis of rotation to create within said centrifugation zone at least partial radial stratification of the constituent parts of the carrier,
means defining a first outlet for withdrawing a first portion of the radially stratified carrier from said centrifugation zone,
means defining a second outlet axially spaced from said first outlet in the direction of movement of the carrier and being operative for withdrawing a second portion of the radially stratified carrier from said centrifugation zone,
means at said second outlet for propagating a fluid convective pattern that originates adjacent to said second outlet and extends axially into said centrifugation zone to at least a region adjacent to said first outlet to remix the constituents parts of the radially stratified carrier and present carrier rich in the preselected constituent for withdrawal at said first outlet.

14. An apparatus according to claim 13 and further comprising
means for reintroducing at least part of the second portion of the radially stratified carrier back into the centrifugation zone.

15. An apparatus according to claim 14 wherein said reintroducing means includes
means defining a path for moving at least part of the second portion of the radially stratified carrier outside of said centrifugation zone and in a direction opposite to the movement of carrier within said centrifugation zone.

16. An apparatus according to claim 13 and further including
means for defining a plurality of said first outlets,
means for defining a plurality of said second outlets associated with said first outlets, and
means at said second outlets for propagating a fluid convective pattern originating adjacent to each of said second outlets and extending axially into said centrifugation zone to at least a region adjacent to the associated one of said first outlets to remix the constituent parts of the radially stratified carrier and present carrier rich in the preselected constituent for withdrawal at each of said first outlets.

* * * * *

UNITED STATES PATENT AND TRADEMARK OFFICE
CERTIFICATE OF CORRECTION

PATENT NO. : 5,053,127
DATED : October 1, 1991
INVENTOR(S) : Donald W. Schoendorfer and Claude E. Berthe It is certified that error appears in the above-identified patent and that said Letters Patent is hereby corrected as shown below:

Column 17, line 68, in Claim 1, between "means" and "into", insert --and extend--.

Column 18, line 60, in Claim 7, after "mechanical", insert --coupling--.

Signed and Sealed this

Twenty-fifth Day of May, 1993

Attest:

MICHAEL K. KIRK

Attesting Officer

Acting Commissioner of Patents and Trademarks